US006492127B2

(12) United States Patent
Goodell et al.

(10) Patent No.: US 6,492,127 B2
(45) Date of Patent: Dec. 10, 2002

(54) LATERAL FLOW TESTING DEVICE WITH ON-BOARD CHEMICAL REACTANT

(75) Inventors: Raegan E. Goodell, Orange, CA (US); Dennis D. Blevins, Laguna Hills, CA (US)

(73) Assignee: Varian, Inc., Palo Alto, CA (US)

( * ) Notice: Subject to any disclaimer, the term of this patent is extended or adjusted under 35 U.S.C. 154(b) by 27 days.

(21) Appl. No.: 09/767,756

(22) Filed: Jan. 23, 2001

(65) Prior Publication Data

US 2002/0098512 A1 Jul. 25, 2002

(51) Int. Cl.[7] .............................................. G01N 33/53
(52) U.S. Cl. ........................ 435/7.1; 435/7.2; 435/7.8; 435/7.92; 435/7.94; 435/7.95; 435/174; 435/970; 435/971; 436/518; 436/514; 436/538; 436/524; 436/530; 436/535; 436/533; 436/810; 436/825; 422/58; 422/56; 422/187; 422/188; 422/104; 422/110; 422/278
(58) Field of Search ........................... 422/58, 56, 187, 422/188, 104, 110, 278; 435/7.1, 7.2, 7.8, 7.92, 7.94, 7.95, 174, 970, 971; 436/518, 524, 538, 530, 535, 533, 810, 825

(56) References Cited

U.S. PATENT DOCUMENTS 4,952,336 A * 8/1990 Brynes et al.
5,770,458 A * 6/1998 Klimov et al.

\* cited by examiner

*Primary Examiner*—Bao-Thuy L. Nguyen
(74) *Attorney, Agent, or Firm*—Walter A. Hackler

(57) ABSTRACT

A lateral flow testing device is provided for testing a biological fluid for the presence of methamphetamines. The device includes a substrate element such as a nitrocellulose strip, including an antibody zone and an immobilized drug conjugate zone for detecting presence of methamphetamines, and an on-board chemical reactant for preventing undesirable cross-reactivity to ephedrine and/or pseudoephedrine that may be present in the biological fluid being tested. Preferably, the on-board chemical reactant is sodium periodate. Methods for preparing test devices are provided including the step of striping a substrate sheet with a solution containing sodium periodate during manufacture of methamphetamine lateral flow test strips.

22 Claims, 1 Drawing Sheet

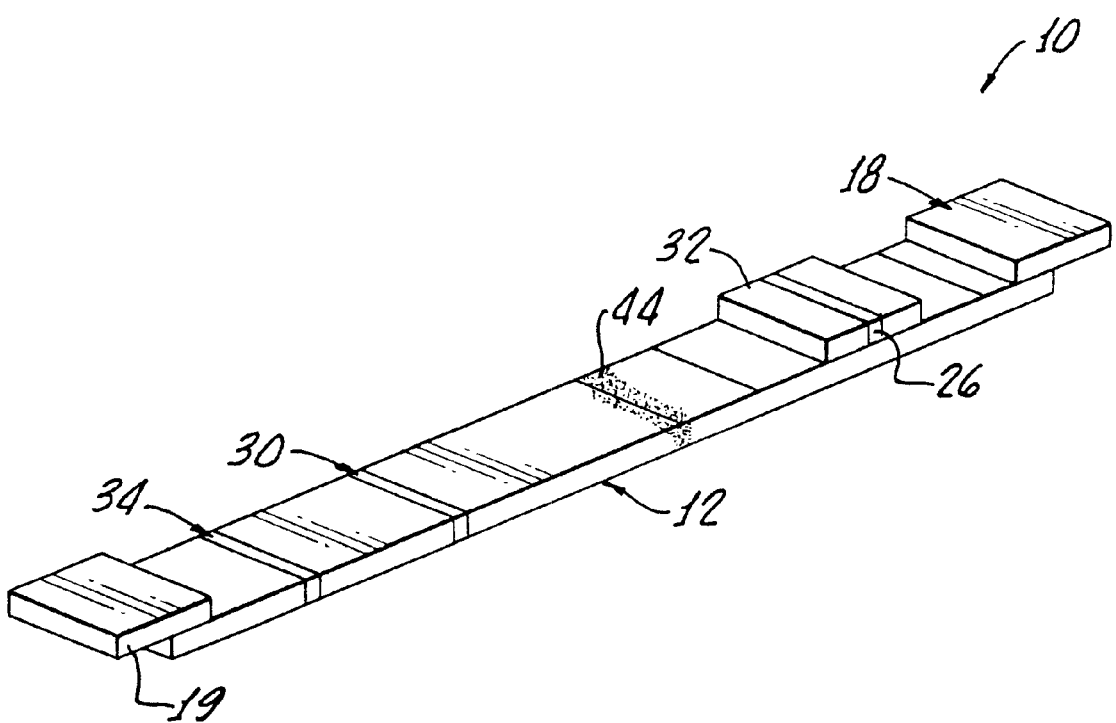

LATERAL FLOW TESTING DEVICE WITH ON-BOARD CHEMICAL REACTANT

The present invention generally relates to a test device and method for testing a biological fluid for the presence of certain "drugs of abuse", and more specifically relates to a lateral flow testing device and method for testing for the presence of methamphetamines in a biological sample and the elimination of undesirable cross-reactivity to other substances that may be present in the sample.

Clinical diagnosis relates, in general, to the determination and measurement of various substances which relate to the health or general status of an individual. Physicians, health care workers and the general public as well are concerned about the presence and levels of various substances in body fluids such as blood, urine, and so forth. Among the substances which have been measured in clinical analysis for a long time are glucose, cholesterol, and various enzymes such as amylase and creatine kinase.

Lateral flow testing devices are widely used for detecting of specific compounds, or analytes, in a biological fluid specimen. One or more reagents are striped onto a solid material, such as a cellulose or paper strip, the reagents being selected as necessary or helpful in detection of the analyte in question. A fluid sample, is deposited onto the strip and will migrate, by capillary action, along the strip where the chemical reactions may take place, depending upon the presence or absence of the analyte, in situ.

Devices for testing for the presence of substances-of-abuse, for example, drugs regulated by law with respect to possession and use, by chemical analysis of a biological fluid sample are well known. In the past, methamphetamines have been detected using a number of techniques, including thin layer chromatography (TLC), gas chromatography (GC), and high performance liquid chromatography (HPLC). These methods generally involve chemical extractions of the drugs, complicated procedures requiring highly trained personnel and lengthy assay times. Thin layer chromatography is labor intensive and lacks sensitivity. Gas chromatography and high performance liquid chromatography each of which is also labor intensive, require highly trained personnel to carry out extractions of the analyte from the biological matrix. In addition, gas chromatography normally requires a derivation step.

More recently, competitive binding immunoassays have been developed for testing a biological fluid for the presence of certain substances of abuse, and these provide a preferable alternative to the physical methods described briefly hereinabove. Immunoassay test devices generally include an absorbent, fibrous strip having one or more reagents incorporated at specific zones on the strip. The fluid sample is deposited on the strip and by capillary action the sample will migrate along the strip, entering specific reagent zones in which a chemical reaction may take place. At least one reagent is included which manifests a detectable response, for example a color change, in the presence of a minimal amount of the substance of interest.

A limitation with lateral flow "drugs of abuse" testing products based on immunoassay technologies is the potential false positive resulting from the client using over the counter products, such as diet substances or sinus relief medications. These products may contain the active substances ephedrine or pseudoephedrine. Several methamphetamine immunoassay based lateral flow testing products will exhibit undesirable cross-reactivity with this group of sympathomimetic amines. This produces a "false" positive initial screening result, which typically requires the fluid sample to be sent to a laboratory for further testing and confirmation of the result. The confirmation laboratory may use several ancillary procedures followed by gas chromatography—mass spectrometry ("GC/MS") analysis in order to address possible cross-reactivity issues. The GC/MS procedure involves chemical extractions of the drugs in question, complicated procedures and requires highly trained personnel.

Pretreatment of a urine sample prior to immunoassay testing in order to reduce the occurrence of false positives has been proposed. For example, U.S. Pat. No. 5,262,333 to Heiman et al., issued on Nov. 16, 1993, discloses a method for determining amphetamine and d-methamphetamines in a urine sample using fluorescence polarization immunoassay techniques. The procedure described in the Heiman, et al. patent includes a step of pretreating the urine sample to eliminate cross-reactivity (i.e. the recognition of compounds other than the desired substance of interest) by preincubating the sample with an aqueous periodate solution having a pH of about 4.5. According to Heiman et al., the described procedure will reduce the occurrence of "false" positives resulting from cross-reactivity for 1-methamphetamine, and other amphetamine-like compounds, commonly occurring in prescriptions and over-the-counter medications.

U.S. Pat. No. 5,573,955, issued on Nov. 12, 1996 to Khanna et al., describes a method for reducing or eliminating tyramine interference from amphetamine and methamphetamine immunoassays, including pretreating the sample with aqueous tyramine oxidase for a time and at a temperature and pH sufficient to deaminate any tyramine present in the sample. The pretreated sample is then applied to an immunoassay test device.

It would be beneficial to have an easy-to-use, inexpensive, reliable device and method for testing a biological fluid specimen for the presence of certain drugs-of-abuse, without the need for complicated, costly confirmation procedures, and without requiring a pretreatment step to reduce or eliminate potential occurrences of "false positive" results. The present invention provides such a device and method.

SUMMARY OF THE INVENTION

Accordingly, devices and methods are provided by the present invention that are useful for detecting a presence of certain substances of abuse, for example methamphetamine, without presenting cross-reactivity issues to other similar substances that may be present in sample.

Particularly, a competitive inhibition assay test device is provided. The device generally comprises a substrate, for example a nitrocellulose test strip having a sample introduction portion and a drug detection portion. Incorporated onto the drug detection portion is means for detecting a presence of methamphetamines in a sample of biological fluid, for example urine. The drug detection means includes a color particle coupled antibody and an immobilized drug conjugate zone. The immobilized drug conjugate zone is in the form of a line on the strip and is retained through physisorption. When a sample is introduced onto the sample pad, it migrates onto the conjugate pad and solubilizes the coupled antibody. The sample and the color tagged antibody travel down the lateral flow strip and is wicked onto an absorbent end pad which serves to drive the sample through the strip via capillary action. The mobilized colored antibody migrates down the strip toward the drug conjugate line. If the antibody recognizes the drug on the drug conjugate line, a portion of the solution is stopped and forms a colored line. The remainder continues to flow down the strip where another portion interacts with a nonspecific "test valid" line. The remainder flows into an end pad connected to the strip. Such methamphetamine test strips as are well known and therefor the details of manufacturing such strips are not included herein.

Importantly, however, unlike conventional methamphetamine test devices, the present device further comprises an additional chemical reagent disposed on-board the substrate strip. This additional chemical reagent provides means for preventing undesirable cross-reactivity caused by the presence of certain active compounds, such as ephedrine and pseudoephedrine, that may be present in the fluid specimen. More specifically, the chemical reagent comprises sodium periodate, applied or striped onto the substrate. The sodium periodate is applied to a portion or zone of the substrate positioned between the antibody zone and the immobilized drug conjugate zone. It has been found that placement of the sodium periodate zone is critical to the effectiveness of the present device. Placement of the sodium periodate zone in a different location on the strip, e.g. prior to the colored particle antibody zone, is ineffective in preventing ephedrine or pseudoephedrine related interference problems.

Advantageously, the present device provides a simple, inexpensive, reliable methamphetamine test strip that will not exhibit so called "false" positive test results, even when used for methamphetamine screening of an untreated urine specimen which contains ephedrine or pseudoephedrine.

BRIEF DESCRIPTION OF THE DRAWING

The present invention will be better understood and appreciated with reference to the following Detailed Description, when considered in conjunction with the accompanying Drawing of which:

FIG. 1 shows a perspective view of a methamphetamine test device in accordance with the invention.

DETAILED DESCRIPTION

Turning now to FIG. 1, a test device 10 in accordance with the invention is shown. The device 10 generally comprises a substrate 12, for example a nitrocellulose test strip, a sample introduction portion, comprising a sample pad 18, and an absorbent end pad 19. A fluid sample, such as a urine specimen, is deposited onto the sample pad 18, and is wicked into the end pad 19 which serves to drive the fluid sample from the sample pad 18 through the length of the strip 12 by capillary action of the nitrocellulose strip 12.

The strip 12 is adapted to provide means for enabling detection of a presence of methamphetamines in a urine specimen deposited on the sample pad 18. More specifically, the device 10 in accordance with the present invention is a competitive inhibition assay type test device. Thus, for example, the drug detection means may include a color particle coupled antibody region 26 and an immobilized drug conjugate zone 30 downstream of the coupled antibody region 26. The immobilized drug conjugate zone 30 exhibits a color change in the absence of the substance of interest (i.e. methamphetamines).

Even more specifically, the antibody region 26, comprises a methamphetamine antibody coupled to a marker agent, preferably a colored particle, for example a particle of gold or dyed latex. The antibody region 26 is directly downstream of the sample pad 18 and may be deposited on a conjugate release pad 32 or may be physically attached to the nitrocellulose strip 12. (See for example, U.S. Pat. No. 5,770,458 to Klimov et al., which is incorporated herein in its entirety by this specific reference.)

The drug conjugate zone 30 comprises a drug conjugate that is immobilized in the form of a line, as shown, on the nitrocellulose strip 12. The drug conjugate is retained on the strip through physisorption or other suitable means. The test device 10 may also comprise a test validity or confirmation zone 34 for indicating whether the fluid solution deposited on the sample pad 18 has migrated through the length of the strip 12 as desired. Processes and materials used in the preparation of competitive inhibition assay methamphetamine test strips are well known, and further detail is therefor not included herein.

Importantly, the device 10 comprises an additional chemical reagent, disposed on-board the substrate 12, which provides means for preventing undesirable cross-reactivity caused by the presence of certain active compounds, particularly ephedrine and/or pseudoephedrine, that may be present in the sample of fluid.

More particularly, the device 10 further comprises a region 44, of the strip 12 that has been treated with a solution containing sodium periodate, wherein the periodate-treated region 44 is disposed between the antibody region 26 and the drug conjugate line 30. The periodate-treated region, sometimes hereinafter referred to as the "periodate zone" 44, contains periodate integrated into the substrate 12 in an amount effective to substantially or completely eliminate ephedrine and pseudoephedrine cross-reactivity in an untreated urine sample.

Specifically, for example, the sodium periodate solution comprises a solution containing about 37 mg/mL sodium periodate, which is applied or striped onto the substrate 12 using conventional means. For example, the sodium periodate is striped onto the substrate at a rate of 1 microliter per centimeter. This represents about 19 micrograms of periodate on a 0.5 cm wide strip (about 0.09 micromoles of periodate per strip).

It is critical that the periodate zone 44 is placed on the strip 12 in a position such that the fluid sample is allowed to interact with the antibody first and then with the periodate line prior to entering the drug conjugate zone 30. It is theorized that without the sodium periodate line, the test fails because ephedrine occupies the antibody active site during migration of the fluid into the drug conjugate line. In a competitive inhibition assay test device, a colored, visible line appearing at the drug conjugate zone 30 indicates a negative test result, a lack of a visible line at the drug conjugate zone indicates a positive test result for the presence of methamphetamines. When ephedrine is present in the sample fluid, the immobilized drug conjugate does not bind with the migrating colored-particle antibody, as the active antibody site is already occupied by ephedrine. Thus, as the colored particle migrates past the drug conjugate line 26, it would not be retained at the immobilized drug conjugate zone, resulting in a "positive" test result even though there may be no methamphetamine in the urine sample.

By providing the periodate line 44 between the color particle coupled antibody zone 26 and the drug conjugate zone 30, it is theorized that during the migration time of the fluid sample containing ephedrine toward the drug conjugate line, the active site on the colored particle coupled antibody is freed from the ephedrine, and thus can now interact with the immobilized drug conjugate in the drug conjugate zone 30. Interestingly, it has been found that if the periodate zone 44 is placed upstream of the antibody zone 26, or if the periodate is placed in the sample pad 18, the test fails.

During testing of the present invention, conventional methamphetamine test strips and methamphetamine test strips having an on-board periodate zone, in accordance with the invention, were challenged. Performance accuracy was measured with urine standards containing the substances ephedrine or pseudoephedrine at high levels, for example about 50,000 ng/mL, but not containing the substance methamphetamine.

As expected, the conventional methamphetamine strips showed a "positive" result, incorrectly indicating the presence of methamphetamine. In contrast, the periodate treated strips, in accordance with the present invention, showed a "negative" result for methamphetamine when challenged with the same urine standard.

Periodate treated strips in accordance with the invention were further tested with urine standards that contained methamphetamine at various levels, particularly at above cut-off level, at cut-off level, and below cut-off level. The urine standards also contained ephedrine and pseudoephedrine at the high levels as previously described. Strip performance accurately indicated the presence of methamphetamine at the appropriate level in the urine sample.

Another set of experiments involved analyzing an authentic urine specimen from a subject person who had ingested a commercially available diet supplement containing ephedrine. Label recommended dosage was followed. Urine specimens were collected from the individual and tested using both on-board periodate lateral flow test strips, in accordance with the invention, and conventional lateral flow test devices for methamphetamine. The conventional devices showed a positive methamphetamine result. The strips in accordance with the present invention indicated a negative result for methamphetamine.

In order to confirm the results, the authentic urine specimen was further tested using conventional laboratory procedures, including GC/MS and broad drug spectrum analysis. The broad drug spectrum analysis was expanded to include sympathomimetic amines special procedure allowing differentiation of pseudoephedrine, phenylpropanolamine, amphetamine, phentermine, and methamphetamine. Each of the confirmation tests on the sample indicated the absence of methamphetamine and the presence of ephedrine.

In addition, a method of preparing a lateral flow testing device for detection of methamphetamines in an untreated fluid sample, is provided by the present invention. The method generally comprises the steps of providing a substrate element, such as a substrate strip or sheet, and treating the element with suitable chemical reagents effective in enabling detection of methamphetamine in a fluid sample applied to the sheet.

More specifically, the step of treating comprises treating a first portion of the substrate element with methamphetamine antibodies, and treating a second portion of the substrate element with an immobilized drug conjugate. Importantly, the inventive method further comprises applying a solution containing sodium periodate to a portion of the substrate sheet positioned between the first portion and the second portion. The sodium periodate is applied in an amount that will be effective to prevent undesirable cross reactivity in presence of ephedrine or pseudoephedrine in the urine sample. The solution may be applied by striping the substrate sheet with a solution of sodium periodate with a concentration of about 37 mg/mL sodium periodate.

In another embodiment of the invention, a completed competitive inhibition methamphetamine lateral flow test element is obtained and is then treated with sodium periodate as described hereinabove, to improve reliability of the test element.

In another embodiment, the substrate sheet may comprise an "in-process" methamphetamine lateral flow test sheet. For example, the sheet may comprise a lateral flow, competitive inhibition assay test sheet that has been treated with chemical reagents effective in enabling detection of methamphetamines in a fluid sample. In this embodiment, the method preferably further comprises the step of cutting the substrate sheet into multiple, individual test strips. The step of cutting is preferably performed after the step of applying the sodium periodate solution.

Although there has been hereinabove described a lateral flow testing device with on-board chemical reactant, and method for manufacturing same, in accordance with the present invention, for the purpose of illustrating the manner in which the invention may be used to advantage, it will be appreciated that the invention is not limited thereto.

For example, although the hereinabove description refers to a lateral flow testing device for detecting methamphetamines in urine, with appropriate modification, the device may be used for detection of methamphetamines in other fluid samples such as a oral fluids, whole blood, blood serum, and plasma.

In addition, although the present description refers to the elimination of ephedrine related cross-reactivity, it should be appreciated that the present invention, with appropriate modification thereto, may be useful for eliminating undesirable cross-reactivity with other substances as well. For example, the present invention may provide a methamphetamine test device including means for reducing tyramine interference. For example, the additional chemical reagent may comprise a tyramine oxidase solution to deaminate any tyramine present in the fluid sample being tested. Accordingly, and all modifications, variations, or equivalent arrangements which may occur to those skilled in the art should be considered to be within the scope of the invention as defined in the appended claims.

What is claimed is:

1. A lateral flow testing device comprising:
   a substrate;
   a drug detector for detecting presence of a desired analyte in a fluid specimen, the drug detector including an antibody zone and a drug conjugate zone, for detecting a presence of methamphetamines in a sample of fluid deposited on the substrate; and
   a chemical reagent zone, disposed on-board the substrate and positioned between the antibody zone and the drug conjugate zone, for preventing undesirable cross-reactivity by substances other than the desired analyte in the fluid sample.

2. The device according to claim 1 wherein the chemical reagent zone comprises a chemical reagent effective in preventing undesirable cross-reactivity to a presence of ephedrine or pseudoephedrine in the sample of fluid.

3. The device according to claim 2 wherein the chemical reagent comprises sodium periodate.

4. The device according to claim 3 wherein the chemical reagent comprises about 19 micrograms of sodium periodate.

5. The device according to claim 1 wherein the antibody zone comprises a methamphetamine antibody.

6. The device according to claim 1 wherein the antibody zone comprises a colored particle-coupled antibody.

7. The device according to claim 1 wherein the antibody zone comprises a methamphetamine antibody coupled to a colored particle.

8. The device according to claim 1 wherein the drug conjugate zone comprises an immobilized drug conjugate.

9. The device according to claim 8 wherein the drug conjugate is retained on the substrate through physisorption.

10. The device according to claim 1 wherein the chemical reagent zone comprises sodium periodate, the antibody zone comprises a colored particle coupled antibody, and the drug conjugate zone comprises an immobilized drug conjugate.

11. A competitive inhibition assay test device comprising:
    a substrate having a length and a sample introduction portion;
    an absorbent end pad, connected to the substrate, for drawing a fluid specimen from the sample introduction portion through the length of the substrate to the absorbent end pad;
    a methamphetamine antibody zone disposed on the substrate downstream of the sample introduction portion;
    a drug conjugate zone disposed on the substrate downstream of the methamphetamine antibody zone; and
    a periodate zone, disposed on the substrate and positioned between the methamphetamine antibody zone and the drug conjugate zone, for substantially eliminating cross reactivity caused by the presence of ephedrine or pseudoephedrine in the fluid specimen.

12. The test device according to claim 11 wherein the methamphetamine antibody zone comprises a colored particle coupled antibody.

13. The test device according to claim 11 wherein the substrate comprises a nitrocellulose strip.

14. The test device according to claim 13 wherein the chemical reagent zone comprises about 19 micrograms of sodium periodate.

15. A method of preparing a lateral flow testing device for detection of methamphetamines in an untreated fluid sample, the method comprising the steps of:
    providing a substrate sheet;
    applying a methamphetamine antibody to a first portion of the sheet;
    applying a drug conjugate to a second portion of the sheet; and
    applying a solution containing sodium periodate to the sheet in a position spaced apart from and between the first portion and the second portion.

16. The method according to claim 15 wherein the step of applying a methamphetamine antibody comprises applying a colored particle coupled antibody.

17. The method according to claim 15 wherein the step of applying a drug conjugate comprises immobilizing the drug conjugate on the substrate.

18. The method according to claim 17 wherein the step of applying a solution comprises applying a solution containing sodium periodate to a third portion of the substrate sheet, wherein the third portion is disposed between the first portion and the second portion.

19. The method according to claim 17 further comprising the step of cutting the substrate sheet into multiple strips.

20. The method according to claim 19 wherein the step of cutting the substrate sheet into strips is performed after the step of applying a solution containing sodium periodate.

21. A method of preparing a lateral flow testing device for detection of methamphetamines in an untreated fluid sample, the method comprising the steps of:
    providing a methamphetamine lateral flow test sheet that has been treated with chemical reagents effective in enabling detection of methamphetamines in a fluid sample;
    applying a solution containing sodium periodate to a portion of the sheet to eliminate undesirable cross reactivity; and
    cutting the sheet into individual methamphetamine test strips.

22. The method according to claim 21 wherein the step of applying a solution comprises striping the substrate sheet with the solution containing sodium periodate.

* * * * *